United States Patent [19]
Krill et al.

[11] Patent Number: 6,048,988
[45] Date of Patent: Apr. 11, 2000

[54] PROCESS FOR THE PRODUCTION OF α-TOCOPHEROL ESTERS

[75] Inventors: Steffen Krill, Speyer; Frank Hübner, Ober-Ramstadt; Rainer Hahn, Karlstein; Horst Weigel, Rodenbach; Klaus Huthmacher, Gelnhausen, all of Germany

[73] Assignee: Degussa-Huls AG, Hanau, Germany

[21] Appl. No.: 09/216,914

[22] Filed: Dec. 21, 1998

[30]  Foreign Application Priority Data

Dec. 20, 1997 [DE] Germany .............................. 197 57 124

[51] Int. Cl.⁷ .................................................. C07D 311/72
[52] U.S. Cl. .............................................................. 549/410
[58] Field of Search ............................................... 549/410

[56]     References Cited

U.S. PATENT DOCUMENTS 3,789,086   1/1974   Frick et al. .

FOREIGN PATENT DOCUMENTS

| 0 694 541 | 1/1996 | European Pat. Off. . |
| 2 259 822 | 8/1975 | France . |
| 51-080859 | 7/1976 | Japan . |

*Primary Examiner*—Laura L. Stockton
*Attorney, Agent, or Firm*—Pillsbury Madison & Sutro LLP

[57]     ABSTRACT

A process for the production of α-tocopherol esters, derivatives or homologs thereof of the general formula

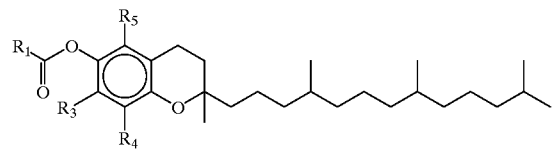

in which the mono- or diester of a hydroquinone is reacted with an allyl alcohol derivative or an allyl alcohol in the presence of zinc halides and proton-liberating acids at a temperature of 25° to 100° C.

14 Claims, No Drawings

PROCESS FOR THE PRODUCTION OF α-TOCOPHEROL ESTERS

FIELD OF THE INVENTION

This invention relates to the production of α-DL-tocopherol esters (vitamin E esters), the derivatives and homologs thereof by reacting diacetylated substituted hydroquinones with phytol and isophytol or the homologs thereof in the presence of catalytically active compounds.

BACKGROUND OF THE INVENTION

Processes are primarily known for the production of α-DL-tocopherol.

α-Tocopherol and the derivatives thereof are significant as feedstuff additives, anti-oxidants, agents to stimulate circulation of the blood, agents to reduce cell aging and for related applications.

According to the prior art, trimethylhydroquinone (TMHQ) is generally used as the starting material, which is reacted with isophytol using various catalyst systems. (DE-OS 4243464=U.S. Pat. No. 5,523,420, DE-OS 19603142, EP 0694 541). Once the reaction is complete, the product must then be completely acetylated in order to obtain, for example, conventional commercial, storage-stable vitamin E acetate. A feature common to all these processes is that they do not directly give rise to tocopherol acetate, the conventional commercial, storage-stable form of vitamin E.

Attempts have also been made to synthesize tocopherols by reacting trimethylhydroquinone ester as the educt with isophytol.

FR-A 2 259822 (DE-OS 2 404621) relates to the use of diacetylated trimethylhydroquinone.

However, the condensation described therein with isophytol in the presence of a solid acid results in a yield of only approx. 41% α-DL-tocopherol and does not give rise to the corresponding esters.

DE-OS 2 160 103 (=U.S. Pat. No. 3,789,086) describes the condensation of trimethylhydroquinone monoacetate with isophytol.

Using Fe(II)Cl$_2$ and hydrochloric acid with simultaneous separation of the water of reaction gives rise to only small quantities of the α-tocopherol acetate and it is necessary to perform post-acetylation with amine catalysis and addition of superstoichiometric quantities of acetic anhydride.

According to JP-OS 51-80859 (15$^{th}$ July 1976), trimethylhydroquinone or the ester thereof is reacted with isophytol in the presence of zinc chloride.

In accordance with the stated object, the reaction gives rise to α-tocopherol at temperatures of greater than 100° C.

SUMMARY OF THE INVENTION

The object of the invention is to provide an improved process for the production of α-DL-tocopherol esters, in which the reaction proceeds in the first stage as far as possible in the direction of the ester.

The present invention provides a process for the production of α-tocopherol esters, the derivatives or homologs thereof of the general formula

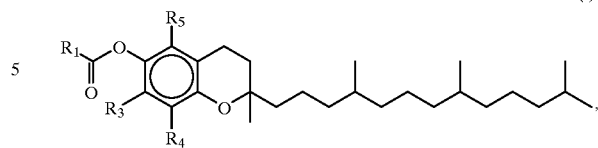

which process is characterized in that the mono- or diesters of a hydroquinone of the general formula

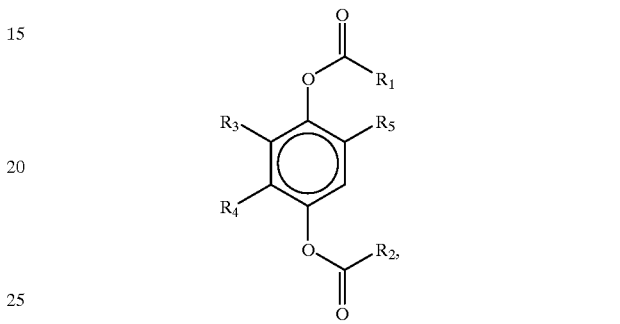

in which
$R_1$, $R_2$ are $C_1$–$C_{20}$ alkyl, branched or unbranched, where $R_1$ and $R_2$ are the same or different, and
$R_3$, $R_4$, $R_5$ are H, $C_1$–$C_3$ alkyl, and are identical or different, are reacted with an allyl alcohol derivative of the general formula

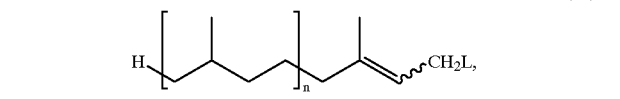

in which n represents a number from 0 to 5 and L represents a hydroxyl, halogen, acetoxy, methanesulfonyloxy, ethanesulfonyloxy, benzenesulfonyloxy or toluenesulfonyl group, or with an allyl alcohol of the general formula

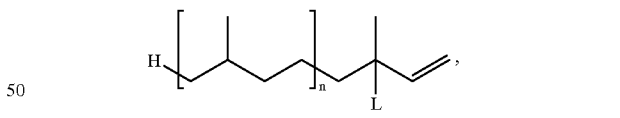

in which n represents the same numbers as above and L represents a hydroxyl, halogen or acetoxy group, in the presence of zinc halides and proton-liberating acids and water at a temperature of 25° to 100° C., preferably 40° to 80° C.

Trimethylhydroquinone diacetate and isophytol are the preferably used reactants.

The diacetate is produced in a particularly suitable process according to EP-A 0808815.

In a preferred embodiment, the dissolved esters of formula (II) together with the zinc halides and the acid are initially introduced and the compound according to formula (III) or (IV) is added to this solution. The water and acetic acid formed in the reaction remain in the reaction mixture and are not removed.

It is unexpected to the person skilled in the art that the desired esters are obtained at such a high concentration despite the acidic medium and the presence of water as a product. After the reaction, unesterified compounds are converted into the desired esters, optionally using known processes, in particular by acetylation with acetic anhydride.

One method which has proved particularly effective is to establish a concentration of water in the reaction mixture of $10^{-2}$ mol. % to 100 mol. %, relative to the introduced TMHQ diacetate. This may be achieved by adding and apportioning aqueous or concentrated protonic acid. Good yields are achieved when hydrochloric acid is used as the protonic acid.

Further suitable acids are sulfuric acid, sulfuric acid/$SO_3$ mixtures having various $SOL_3$ concentrations, trifluoromethanesulfonic acid and corresponding superacids having an $H_0$ value of less than or equal to −11.9, in particular also mixtures of boric acid and oxalic acid, generally in a molar ratio of 1:1 to 1:5, in particular of 1:2.

They are generally used in a concentration of $10^{-2}$ to 100 mol. %, relative to TMHQ diacetate.

Zinc halides, in particular zinc chloride or zinc bromide, are in particular used in a concentration of 10 to 100 mol. %, relative to trimethylhydroquinone diacetate. Although no particular restrictions apply with regard to the quantity of solvent used, 0.1 to 100 ml/g of TMHQ diacetate are preferably used, wherein 1 to 10 ml/g are particularly suitable.

In a preferred embodiment, the starting material of formula (II), the catalyst mixture comprising Lewis acid and Brønsted acid and the organic solvent are initially introduced and the compounds according to formulas (III) or (IV) are then added.

After the reaction, the desired product is isolated and esterification using known methods is optionally also performed.

Organic solvents suitable for the reaction are carbonate esters, such as for example dimethyl carbonate,
diethyl carbonate,
dipropyl carbonate,
methylethyl carbonate,
ethylene carbonate and
propyl carbonate or carboxylic acid esters, such as for example n-propyl acetate,
i-propyl acetate,
n-butyl acetate,
i-butyl acetate,
t-butyl acetate,
n-amyl acetate,
i-amyl acetate [$CH_3COOCH_2CH_2CH(CH_3)_2$],
sec-amyl acetate [$CH3COOCH(CH_3)CH_2CH_2CH_3$],
t-amyl acetate [$CH_3COOC(CH_3)_2CH_2CH_3$],
2,2-dimethylpropyl acetate [$CH_3COOCH_2C(CH_3)_3$],
2-methylbutyl acetate [$CH_3COOCH_2CH(CH_3)CH_2CH_3$],
methyl propionate,
n-butyl propionate,
ethyl butyrate,
i-propyl butyrate,
methyl isobutyrate,
ethyl isobutyrate,
i-butyl isobutyrate,
methyl valerate,
ethyl valerate,
methyl isovalerate,
ethyl isovalerate, n-propyl acetate, i-propyl acetate, n-butyl acetate, i-butyl acetate, n-butyl propionate, ethyl butyrate, i-propyl butyrate, methyl isobutyrate, ethyl isobutyrate, methyl valerate are particularly suitable, or non-polar solvents, such as for example pentane, hexane, heptane, octane,
ligroin, petroleum ether, cyclohexane,
benzene, toluene and xylene.

or aliphatic alcohols, such as for example methanol,
ethanol,
n-propanol,
i-propanol,
n-butanol,
i-butanol,
t-butanol,
n-amyl alcohol (1-pentanol),
2-pentanol (1-methyl-1-butanol)
3-pentanol (1-ethyl-1-propanol)
i-amyl alcohol (3-methyl-1-butanol)
t-amyl alcohol (1,1-dimethyl-1-propanol)
2,2-dimethyl-1-propanol,
1,2-dimethyl-1-propanol,
2-methyl-1-butanol, and
3-methyl-2-butanol.

n-Propanol, i-propanol, n-butanol, i-butanol, t-butanol, n-amyl alcohol, 2-pentanol, 3-pentanol, i-amyl alcohol and t-amyl alcohol, together with mixtures prepared from the stated groups of solvents are particularly preferred. In mixtures, one of the solvents acts as a cosolvent.

The use of cyclic carbonates, such as inter alia ethylene carbonate or propylene carbonate, open-chain esters of acetic acid, such as ethyl acetate, propyl acetate, butyl acetate and isobutyl acetate has a particular influence upon selectivity.

It is also possible to perform the cyclocondensation reaction in liquid or supercritical carbon dioxide as the solvent. There is also nothing to prevent continuous performance of the reaction with recycling of the catalyst in a suitable solvent.

The advantageous results of the simply performed synthesis according to the invention of DL-α-tocopherol or DL-α-tocopherol acetate from trimethylhydroquinone di- or monoacetate and isophytol or the compounds stated in claim 1 in the presence of a protonic acid and zinc halides are in particular unexpected because according to the prior art, the water of condensation formed during the reaction is conventionally removed from the system. However, in contrast, in the process according to the invention, water performs a catalytic function and is necessary if the reaction is to proceed selectively.

The process according to the invention additionally considerably simplifies the conventional method as it has been found that, unlike in the prior art, an esterified TMHQ is used, the ester group of which is retained to an unexpectedly large extent in the final product according to the formula (I). Economies of acetic anhydride may accordingly be made in the subsequent acetylation.

On the other hand, it is also possible to saponify the crude product of the reaction, so forming DL-α-tocopherol as the final product.

It has thus proved possible to develop a tocopherol acetate synthesis into an industrially practicable, economically viable process while reducing the number of reaction stages and making economies of raw materials.

DETAILED DESCRIPTION OF THE PREFERRED EMBODIMENTS

PRACTICAL EXAMPLES

Practical Example 1
Synthesis of α-DL-tocopherol acetate

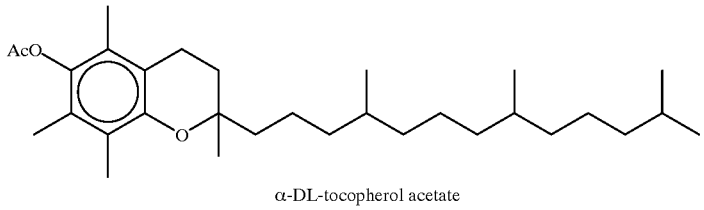

α-DL-tocopherol acetate

A mixture of 10.9 g (=46 mmol) of trimethylhydroquinone 1,4-diacetate (GC: 100%), 5.2 g (=38.17 mmol=83 mol. %, relative to TMHQ-DA) of $ZnCl_2$ and 0.65 ml of $HCl_{conc.}$ in 15 ml of hexane, 0.7 ml of n-butanol and 15 ml of n-propyl acetate is heated to 60° C. 14.5 g (=48 mmol) of isophytol (GC:>98%) is added dropwise to this solution within 4 hours. Once addition is complete, stirring is continued for a further 2 hours at 60° C. Once the reaction is complete, the mixture is cooled to room temperature and 100 ml of petroleum ether is added to the resultant reaction mixture. The solution is washed with 2×20 ml of water and 2×20 ml of saturated $NaHCO_3$ solution. The organic phase is then separated, dried over magnesium sulfate and, after filtration of the salt, the solvent is stripped out in a rotary evaporator. 21 g of a yellow oil are obtained, which, according to HPLC analysis, is of the following composition: 28 wt. % vitamin E (=5.88 g), 65.8 wt. % vitamin E acetate (=13.82 g), 1.6 wt. % (=0.34 g) TMHQ monoacetate. After converting the free vitamin E content into vitamin E acetate equivalents, the total yield of tocopherol acetate is found to be 20.27 g, corresponding to 93.2% of theoretical. Conversion of TMHQ diacetate is quantitative.

Practical Example 2
Synthesis of tocopherol acetate from TMHQ-DA

The same method is used as described in Example 1 and 10.9 g (=46 mmol) of TMHQ diacetate is initially introduced in 15 ml of isobutyl acetate. 0.63 ml of concentrated hydrochloric acid and 5.2 g (=38.17 mmol) of $ZnCl_2$ are added to this solution. The isophytol (14.5 g=48 mmol) is added at 60° C. within 6 hours. After conventional working up, 21.7 g of a brown crude product are obtained which, according to HPLC, has the following composition: 37.6 wt. % tocopherol and 54.4 wt. % tocopherol acetate. TMHQ diacetate conversion is 100% and 0.74 wt. % of TMHQ-MA is still detected. This corresponds to a yield of 11.8 g of vitamin E acetate and 8.16 g of vitamin E. After converting the vitamin E yield into vitamin E acetate equivalents, this corresponds to a yield of 95.45%. At TMHQ-MA conversion of 98.17%, selectivity for vitamin E is 42%. Selectivity for vitamin E acetate is 55.3%. Overall selectivity for the desired products is thus 97.3%.

Practical Example 3
Synthesis of tocopherol acetate from TMHQ-MA

The same method is used as in the preceding Example 2, except that, instead of the diacetate, the TMHQ monoacetate obtained therefrom by selective saponification is used. 5.2 g (38.17 mmol) of $ZnCl_2$ and 8.9 g (=45.8 mmol) of TMHQ monoacetate are initially introduced in 15 ml of ethyl acetate, 0.63 ml of concentrated HCl are added to this mixture and the mixture heated to 60° C. 13.8 g (=46.5 mmol) of isophytol are continuously added dropwise over 2.5 hours. The reaction is allowed to continue for a further 2.5 hours at 50° C. After conventional working up, a brown oil is obtained which, according to quantitative HPLC analysis, is of the following composition: 4.83 wt. % TMHQ-MA, 18 wt. % vitamin E and 66.9 wt. % vitamin E acetate. The final weight amounts to 21.0 g. This corresponds to a yield of 84%. Conversion is 88.6% and selectivity for tocopherol and tocopherol acetate is 94.8%.

Practical Example 4
Synthesis of tocopherol acetate from TMHQ-DA

The same sequence of addition of the components is used as in Example 1 and 5.2 g (38.17 mmol) of $ZnCl_2$ and 0.65 ml of concentrated HCl and 10.9 g (=46.1 mmol) of TMHQ-DA are initially introduced in 15 ml of n-propyl acetate. 14.5 g (=48.9 mmol) of isophytol are added at 50° C. within 4.5 hours and stirring is continued for 1.5 hours. After conventional working up, 19.3 g of a honey-coloured oil are obtained which, according to HPLC analysis, has the following contents of tocopherol and the acylated form thereof: 15.8 wt. % of vitamin E, 64.5 wt. % of vitamin E acetate. Once the quantity of vitamin E formed has been converted into the equivalent quantity of vitamin E acetate, this corresponds to a yield of 72.5%.

Practical Example 5
Synthesis of α-tocopherol acetate

The same method is used as described in Example 4, with the same stoichiometric ratio of the educts, but using 15 ml of isobutyl acetate as the solvent instead of n-propyl acetate and adding 0.83 ml of water to the reaction mixture. After 6 hours' reaction time at 50° C., the mixture is worked up in the usual manner and a product is obtained in the form of a light brown oil which, according to HPLC, consists of 20.1 wt. % of vitamin E and 67.71 wt. % of vitamin E acetate. The corresponding monoacetate is detected at a content of 2.0 wt. %. Yield is thus 90% of theoretical.

Practical Example 6
Synthesis of α-tocopherol acetate

The same method is used as described in Example 3 and 5.2 g (=38.17 mmol) of $ZnCl_2$ and 8.9 g (=45.8 mmol) of TMHQ monoacetate are initially introduced in 15 ml of methyl isobutyl ketone, 0.63 ml of concentrated HCl are added to this mixture and the mixture heated to 35–40° C. While maintaining this temperature, 13.8 g (=46.5 mmol) of

7 isophytol are apportioned within 2.5 hours and stirring is continued for a further 2.5 hours. Once cool, the mixture is washed with 10 ml of water. 60 ml of toluene are added to the organic phase, the mixture washed with 20 ml of a 2% NaOH solution, rewashed successively with 20 ml portions of water, dried and finally evaporated in a rotary evaporator. 19.1 g of a brown, syrupy oil are obtained which, according to quantitative HPLC determination, has an α-tocopherol acetate content of 47.7 wt. %. This corresponds to a yield of 42.1%. At a conversion of 85.4%, this corresponds to a selectivity of TMHQ-MA to tocopherol acetate of 49.3%. Only trace quantities of free tocopherol are detected.

Practical Example 7
Synthesis of α-tocopherol acetate from TMHQ-MA

The same method is used as described in Example 3 and 5.2 g (=38.17 mmol) of $ZnCl_2$ and 8.9 g (=45.8 mmol) of TMHQ monoacetate are initially introduced in 15 ml of methyl isobutyl ketone, 0.63 ml of concentrated HCl are added to this mixture and the mixture heated to 50° C. While maintaining this temperature, 13.8 g (=46.5 mmol) of isophytol are apportioned within 2.5 hours and stirring is continued for a further 2.5 hours. Once cool, the mixture is washed with 10 ml of water. 60 ml of toluene are added to the organic phase, the mixture washed with 20 ml of a 2% NaOH solution, rewashed successively with 20 ml portions of water, dried and finally evaporated in a rotary evaporator. 21.7 g of a brown, syrupy oil are obtained which, according to quantitative HPLC determination, has an α-tocopherol content of 13.15 wt. %, while the content of tocopherol acetate is 80.42 wt. %. After converting the vitamin E content into the corresponding vitamin E acetate equivalent thereof, this gives a yield of 20.58 g or 95.1%.

Practical Example 8
Synthesis of α-tocopherol acetate from TMHQ-DA

The same method is used as described in Example 1, but, instead of using $HCl_{conc.}$ as the protonic acid, $HCl_{gas}$ is continuously introduced into the reaction solution during the period of the reaction and a water separator is used to remove the water of reaction from the system. 9.2 g (=67.5 mmol=68.4 mol. % relative to TMHQ-DA) of $ZnCl_2$ and 23.6 g (=98.62 mmol) of TMHQ diacetate are initially introduced in 100 ml of toluene, 0.17 g of octadecylamine are added to this mixture and the mixture heated to reflux temperature. While maintaining this temperature, 29.6 g (=99.8 mmol) of isophytol are apportioned within 2.5 hours and stirring is continued for a further 2.5 hours. HCl is introduced into the reaction solution during apportionment of isophytol and the post-reaction time. The mixture is cooled, the crude mixture redissolved in 400 ml of petroleum ether and washed in the conventional sequence with appropriate quantities of water and $NaHCO_3$ solution. The resultant organic phase is evaporated in a rotary evaporator. 41.0 g of a brown, syrupy oil are obtained which, according to quantitative HPLC determination, has an α-tocopherol content of 2.9 wt. %, while the content of tocopherol acetate is 69.5 wt. %. After converting the vitamin E content into the corresponding vitamin E acetate equivalent thereof, this amounts to a yield of 29.8 g or 63.9%.

Comparative Example 1 according to EP 0 694 541
Synthesis of α-Tocopherol from TMHQ The method described in the patent is used and 23.3 g (=153 mmol) of TMHQ and 17.5 g (=129 mmol) of $ZnCl_2$

8 and 2.2 ml of $HCl_{conc.}$ are initially introduced in 54 ml of methyl isobutyl ketone as the solvent. 46.1 g (=153 mmol) of isophytol are added to this solution over a period of 3 hours. The reaction temperature is 25–30° C. and the reaction time 5 hours. After conventional working up, the product is obtained as a brown oil with a final weight of 61.8 g. According to determination of content by means of quantitative HPLC, the oil has an α-tocopherol content of 91.4 wt. %. This corresponds to a yield of 78.1%.

Practical Examples 9–13

Synthesis of α-tocopherol acetate

The following tests were performed in order to investigate the influence of a cosolvent to the heptane used as the solvent. The method described in Example 1 is used, but using $HBr_{conc.}$ as the protonic acid; no water of condensation or acetic acid is removed from the system. 8.6 g (=38.2 mmol =82.9 mol. % relative to TMHQ-DA) of $ZnBr_2$ and 10.9 g (=46.1 mmol) of TMHQ diacetate are initially introduced in 10 ml of heptane. Depending upon the test, 1 ml of the particular alcohol is added as cosolvent. 1.3 ml of 47% HBr (=11.49 mmol=24.9 mol. %) are added to this mixture. 105 mol. % (=14.5 g=48.9 mmol) of isophytol are then apportioned at 60° C. over a period of 1.5 hours. While maintaining this temperature, stirring is continued for 2 hours. The mixture is cooled and worked up as usual. The following table shows yields and contents of vitamin E and vitamin E acetate from this series of tests:

| Cosolvent | Final weight [g] | Vit. E content [wt. %] | Vit. E acetate content [wt.] | Overall yield [% of theoretical] |
|---|---|---|---|---|
| / | 20.9 | 40.3 | 53.2 | 93.9 |
| n-butanol | 21.5 | 45.5 | 49.2 | 97.8 |
| 1-pentanol | 22.6 | 32.5 | 60.7 | 93.9 |
| 2-pentanol | 22.2 | 23.3 | 66.0 | 93.2 |
| 3-pentanol | 23.0 | 19.4 | 68.4 | 94.6 |

Practical Examples 14–21

Synthesis of α-tocopherol acetate

The following tests were performed in order to investigate the influence of $ZnCl_2$ concentration. The same method is used as described in Example 1, but using $HCl_{conc.}$ as the protonic acid; no water of condensation or acetic acid which is formed is removed from the system. The quantities of $ZnCl_2$ stated in the following table and 10.9 g (=46.1 mmol) of TMHQ diacetate are initially introduced in isobutyl acetate. 0.63 ml of 37% HCl are added to this mixture. 105 mol. % (=14.5 g=48.9 mmol) of isophytol are then apportioned at 60° C. over a period of 4.0 hours. While maintaining this temperature, stirring is continued for 2 hours. The mixture is cooled and worked up as usual. The following table shows yields and contents of vitamin E and vitamin E acetate from this series of tests:

| Quantity of ZnCl$_2$ [mol. %] | Quantity of ZnCl$_2$ [g] | Vit. E/ Vit. E-Ac ratio | Vit. E content [wt. %] | Vit. E acetate content [wt. %] | Final weight [g]* | Conversion [%] | Yield** |
|---|---|---|---|---|---|---|---|
| 0.0 | 0.0 | 99:1 | 8.3 | 0.14 | 17.4 | 28.5 | 7.4 |
| 15.9 | 1.0 | 23:77 | 14.7 | 53.9 | 22.6 | 81 | 72.6 |
| 25.4 | 1.6 | 35:65 | 25.6 | 65.2 | 21.0 | 98.3 | 85.4 |
| 41.4 | 2.6 | 33:67 | 28 | 62.3 | 21.3 | 97.3 | 91.0 |
| 51 | 3.2 | 31:69 | 25.9 | 61.8 | 21.2 | 97.3 | 92.5 |
| 63.5 | 4.0 | 34:66 | 28.9 | 61.7 | 22.1 | 99.0 | 94.8 |
| 82.9 | 5.2 | 43:57 | 37.6 | 54.4 | 21.7 | 99.3 | 95.4 |
| 100 | 6.3 | 28:72 | 22.1 | 62.5 | 21.8 | 98.3 | 98.3 |

*Crude product consisting of TMHQ-DA, TMHQ-MA, vitamin E, vitamin E acetate
**For the purposes of determining yield, the content of vitamin E was converted into vitamin E acetate equivalents.
Standard test:
10.9 g TMHQ-DA (100%) = 46.1 mmol 14.5 g isophytol (BASF: GC: >98%) = 48.9 mmol
Protonic acid: 0.63 ml HCl$_{conc.}$. Lewis acid: X g ZnCl$_2$, temperature: 60° C., reaction time: 6 h Practical Examples 22–28
Synthesis of α-tocopherol acetate The following tests were performed in order to investigate the influence of ZnBr$_2$ concentration. The same method is used as described in Examples 16–21 using HBr$_{conc.}$ as the protonic acid. No water of condensation or acetic acid which is formed is removed from the system. The quantities of ZnBr$_2$ stated in the following table and 10.9 g (=46.1 mmol) of TMHQ diacetate are initially introduced in a solvent mixture of heptane and butanol. 1.3 ml of 47% HBr are added to this mixture. 105 mol. % (=14.5 g=48.9 mmol) of isophytol are then apportioned at 60° C. over a period of 2.0 hours. While maintaining this temperature, stirring is continued for 2 hours. The mixture is cooled and worked up as usual. The following table shows yields and contents of vitamin E and vitamin E acetate from this series of tests:

| Quantity of ZnBr$_2$ [mol. %] | Quantity of ZnBr$_2$ [g] | Vit. E/ Vit. E-Ac ratio | Vit. E content [wt. %] | Vit. E acetate content [wt. %] | Final weight [g]* | Conversion [%] | Yield** |
|---|---|---|---|---|---|---|---|
| 10 | 1.04 | 32:68 | 19.34 | 44.24 | 22.5 | 97.4 | 67.6 |
| 20 | 2.08 | 31:69 | 25.57 | 63.71 | 22.2 | 99.3 | 93.5 |
| 30 | 3.11 | 37:63 | 31.92 | 58.62 | 22.1 | 100 | 94.9 |
| 40 | 4.16 | 44:56 | 37.66 | 53.62 | 21.6 | 100 | 93.6 |
| 60 | 6.22 | 30:70 | 25.98 | 66.0 | 21.5 | 100 | 93.2 |
| 80 | 8.32 | 36:64 | 30.85 | 60.2 | 22.2 | 100 | 95.8 |
| 100 | 10.38 | 40:60 | 34.31 | 55.41 | 22.1 | 100 | 94.3 |

*Crude product consisting of TMHQ-DA, THMQ-MA, vitamin E, vitamin E acetate
**For the purposes of determining yield, the content of vitamin E was converted into vitamin E acetate equivalents.
Standard test:
10.9 g TMHQ-DA (100%) = 46.1 mmol 14.5 g isophytol (BASF: GC: >98%) = 48.9 mmol
Protonic acid: 1.3 ml Hbr$_{conc.}$ Lewis acid: X g ZnBr$_2$. Temperature: 60° C. Reaction time: 4 h, Solvent: 15 ml heptane; 1.5 ml n-butanol Practical Examples 29–38
Synthesis of α-tocopherol acetate The following tests were performed in order to investigate the influence of the nature of the protonic acid in the presence of zinc bromide as the Lewis acid. Both mineral acids and organic acids were included in the investigation. The tests were performed as follows: TMHQ-DA is initially introduced in 15 ml of heptane and 1.5 ml of butanol as cosolvent and the appropriate quantity of aqueous acid and ZnBr$_2$ as the Lewis acid are added. The mixture is heated to 60° C. in a water bath and, after a preliminary period of 15 minutes, isophytol is added continuously over a period of 3 hours. After a further 3 hours' post-reaction, the mixture is worked up in the conventional manner. The following table shows the yields and conversions achieved in this manner:

| Lewis acid | Type of protonic acid | Conc. [mol. %]* | $H_2O$ conc. [mol. %]* | Yield [%]** | Conversion [%] | Vit. E/ Vit. E-Ac [mol.:mol.] |
|---|---|---|---|---|---|---|
| $ZnBr_2$ | $HCl_{conc.}$ (= 37%) | 25 | 86 (≡ 0.95 ml) | 91.7 | 99.9 | 48:52 |
| $ZnBr_2$ | $HBr_{conc.}$ (= 47%) | 25 | 126 (≡ 1.35 ml) | 92.2 | 99.8 | 51:49 |
| $ZnBr_2$ | $HI_{conc.}$ (= 57%) | 25 | 134 (≡ 1.52 ml) | 91.7 | 99.9 | 50:50 |
| $ZnBr_2$ | $H_2SO_4$ (30%) | 25 | 319 (≡ 3.1 ml) | 92.9 | 99 | 60:40 |
| $ZnBr_2$ | $H_2SO_4$ (60%) | 25 | 91 (≡ 1.26 ml) | 89.5 | 99.8 | 47:53 |
| $ZnBr_2$ | $NaHSO_4$ (= 70%) | 25 | 84 (≡ 2.29 g) | 79.4 | 98.4 | 22:78 |
| $ZnBr_2$ | $CF_3SO_3H$ (30%) | 25 | 482 (≡ 5 ml) | 83.8 | 98.9 | 44:56 |
| $ZnBr_2$ | $Cl_3CO_2H$ (= 70%) | 25 | 96 (≡ 2.68 g) | 32.2 | 69.6 | 2:98 |
| $ZnBr_2$ | $Cl_3CO_2H$ (100%) | 50 | 0 (≡ 3.77 g) | 41.2 | 71.5 | 3:97 |
| $ZnBr_2$ | $H_3PO_4$ (= 60%) | 25 | 91 (≡ 1.32 ml) | 68.2 | 88.6 | 29:71 |

*relative to introduced TMHQ-DA, figure in brackets relates to introduced aqueous acid
**calculated as overall vitamin E acetate yield (before distillation)
Standard test:
10.9 g TMHQ-DA (100%) = 46.1 mmol 15 ml heptane, 1 ml ultra-pure butanol, 8.6 g $ZnBr_2$ (= 38.2 mmol = 82.9 mol. %), 14.5 g isophytol (BASF: GC: >98%) = 48.9 mmol
Reaction temperature: 60° C.

Practical Examples 39/40

Synthesis of α-tocopherol acetate

TMHQ-DA, Lewis acid and the protonic acid are initially introduced into appropriate quantities of propylene carbonate. The mixture is heated to 60° C. in a water bath and, after a preliminary period of 15 minutes, isophytol is added continuously over a period of 3 hours. The stoichiometric ratio of TMHQ-DA/isophytol is 3:1 in this series of tests. The quantity of solvent is varied. After a further 3 hours' post-reaction, the propylene carbonate phase is extracted with petroleum ether. Both phases are analysed. Unreacted TMHQ esters in the propylene carbonate phase may be reused. The following table shows the yields and conversions achieved in this manner:

| Solvent [ml] | $ZnCl_2$ [mol. %] | $H^+$ conc. [mol. %]** | $H_2O$ conc. [mol. %] | Yield [%]*** | IP conversion | TMHQ ester reten- | Vit. E/ Vit. E-Ac [mol.:mol.] |
|---|---|---|---|---|---|---|---|
| 20 | 40 | 25 | 85 (≡ 0.7) | 89.9 | 100 | 92 | 3:97 |
| 60 | 40 | 25 | 85 (≡ 0.7) | 80.2 | 100 | 89 | 3:97 |

*relative to introduced isophytol;
**concentration of Brønsted acid relative to isophytol;
***calculated as overall vitamin E acetate yield (before distillation)
Initial weights:
32.7 g = 138 mmol TMHQ-DA; 13.8 g = 46 mmol isophytol; 2.5 g $ZnCl_2$ (= 18.4 mmol = 82.9 mol. %), 1.12 ml $HCl_{conc.}$ Practical Examples 41–45

Synthesis of α-tocopherol acetate

TMHQ-DA, Lewis acid and the protonic acid are initially introduced in propylene carbonate. The mixture is heated in a water bath and, after a preliminary period of 15 minutes, isophytol is added continuously over a period of 3 hours. This series of tests is performed with a 5 mol. % excess of isophytol relative to TMHQ-DA. After a further 3 hours' post-reaction, the propylene carbonate phase is extracted with petroleum ether. The stated yields disregard any vitamin E or vitamin E acetate in the propylene carbonate phase. The following table shows the yields and conversions achieved in this manner:

| $ZnCl_2$ [mol. %] | H+ conc. [mol. %]* | Temperature [° C.] | Yield [%]** | IP conversion [%] | Vit. E/ Vit. E-Ac [mol.:mol.] |
|---|---|---|---|---|---|
| 40 | 25 | 60 | 81.54 | 100 | 52:48 |
| 40 | 25 | 100 | 78.4 | 100 | 85:15 |
| 40 | 12.5 | 60 | 78.4 | 100 | 39:61 |
| 40 | 12.5 | 80 | 79.8 | 100 | 54:46 |
| 40 | 12.5 | 100 | 75.2 | 100 | 68:32 |

*Concentration of Brønsted acid relative to TMHQ-DA;
**Calculated as overall vitainin E acetate yield (before distillation), relative to TMHQ-DA.
Initial weights:
10.9 g = 46 mmol TMHQ-DA; 14,75 g = 49 mmol isophytol; 2.5 g $ZnCl_2$ (= 18.4 mmol), 0.62 g $H_2O$ (= 75 mol. % $H_2O$); H+ cat. = $H_3BO_3/C_2O_4H_2$ (molar: 1:2) = 12.5–25 mol. %

Practical Examples 46–51

Synthesis of α-tocopherol acetate

The following tests were performed in order to document the influence of $H_2O$ concentration and Brønsted acid concentration in the presence of zinc bromide as the Lewis acid. The tests were performed as follows: TMHQ-DA is initially introduced in 15 ml of heptane and 1.5 ml of butanol as cosolvent and the appropriate quantity of aqueous acid and $ZnBr_2$ as the Lewis acid are added. The mixture is heated to 60° C. in a water bath and, after a preliminary period of 15 minutes, isophytol is added continuously over a period of 3 hours. After a further 3 hours' post-reaction, the mixture is worked up in the conventional manner. The following table shows the yields and conversions achieved in this manner:

| Lewis acid (mol. %) | Type of protonic acid | Conc. [mol. %]* | $H_2O$ conc. [mol. %]** | Yield [%]*** | Conversion [%] | Vit. E/ Vit. E-Ac [mol.:mol.] |
|---|---|---|---|---|---|---|
| $ZnBr_2$ (82.9) mol. %) | $CF_3SO_3H$ | 25 | 482 | 83.8 | 98.9 | 44:56 |
| $ZnBr_2$ (82.9) mol. %) | $CF_3SO_3H$ | 25 | 96 | 94.5 | 100 | 45:55 |
| $ZrBr_2$ (82.9) mol. %) | $CF_3SO_3H$ | 10 | 96 | 97.1 | 100 | 46:54 |
| $ZnBr_2$ (82.9) mol. %) | $CF_3SO_3H$ | 10 | 48 | 90.1 | 100 | 29:71 |
| $ZnBr_2$ (82.9) mol. %) | $CF_3SO_3H$ | 5 | 96 | 82.7 | 97.3 | 15:85 |
| $ZnBr_2$ (82.9) mol. %) | $CF_3SO_3H$ | 5 | 48 | 80.6 | 97.1 | 17:83 |

*relative to introduced TMHQ-DA, figure in brackets relates to introduced aqueous acid;
**relative to introduced TMHQ-DA;
***calculated as overall vitamin E acetate yield (before distillation)
Standard test:
10.9 g TMHQ-DA (100%) = 46.1 mmol; 15 ml heptane, 1 ml ultra-pure butanol; 8.6 g $ZnBr_2$ (= 38.2 mmol = 82.9 mol. %); 14.5 g isophytol (BASF: GC: >98%) = 48.9 mmol Comparative Example 2

Preparation of DL-α-tocopherol acetate according to JP-OS Sho 51-80859 at 125° C.

15.5 g (=65.6 mmol) of TMHQ-DA and 12.0 g (=88 mmol) of zinc chloride in 20 ml of butyl acetate are initially introduced into a 200 ml three-necked flask fitted with a stirrer, reflux condenser, thermometer and dropping funnel.

The resultant mixture is refluxed under a stream of nitrogen, wherein the reflux temperature is 125° C. 37.7 g (=127.3 mmol) of isophytol, which are dissolved in a further 10 ml of butyl acetate, are added dropwise to this boiling mixture within 50 minutes. The reaction is continued for a further 4 hours with refluxing. Once the reaction is complete, the reaction mixture is extracted with water, wherein the zinc chloride passes into the aqueous phase and a tocopherol/tocopherol acetate mixture remains in the organic phase. According to analysis by gas chromatography, TMHQ-DA conversion is complete, the crude yield of tocopherol is 22.5%, the yield of tocopherol acetate is 45.8%, so giving an overall yield of tocopherol/ tocopherol acetate of 68% relative to TMHQ-DA.

Comparative Example 3
Preparation of DL-α-tocopherol acetate according to JP-OS Sho 51-80859 at 60° C. (catalyst=ZnCl₂ without protonic acid)

The same method is used as described in Comparative Example 2, except that the reaction temperature is reduced to 60° C. After working up in the conventional manner, according to analysis by gas chromatography of the organic constituents of the mixture, 100% of the starting material TMHQ-DA is recovered. The reaction thus does not proceed under these conditions.

What is claimed is:

1. A process for the production of α-tocopherol esters, derivatives or homologs thereof of the general formula

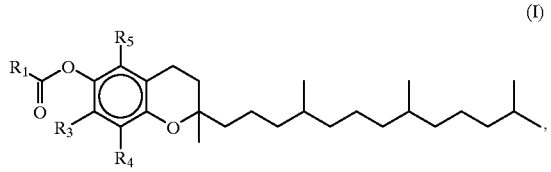

comprising reacting the mono- or diesters of a hydroquinone of the general formula

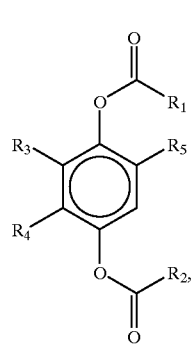

in which
R₁, R₂ are C₁–C₂₀ alkyl, branched or unbranched, saturated or unsaturated, and
R₃, R₄, R₅ are H, C₁–C₃ alkyl, identical or different,
with an allyl alcohol derivative of the general formula

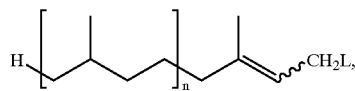

in which n represents a number from 0 to 5 and L represents a hydroxyl, halogen, acetoxy, methanesulfonyloxy, ethanesulfonyloxy, benzenesulfonyloxy or toluenesulfonyl group, or with an allyl alcohol of the general formula

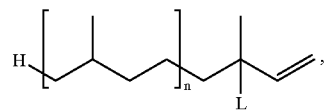

in which n represents the same numbers as above and L represents a hydroxyl, halogen or acetoxy group, in the presence of zinc halide and proton-liberating acid at a temperature of 25° to 100° C.

2. The process according to claim 1, wherein the reaction is performed in the presence of $10^{-2}$ to 100 mol. % of zinc halide, relative to the diester.

3. The process according to claim 2, wherein the diester is a diacetate.

4. The process according to claim 3, wherein the diacetate is TMHQ diacetate.

5. The process according to claim 1, wherein the proton-liberating acid used is a member selected from the group consisting of hydrochloric acid, hydrobromic acid, sulfuric acid, trifluoromethanesulfonic acid and a mixture of boric acid and oxalic acid.

6. The process according to claim 4, the proton-liberating acid is used in a concentration of 1 to 100 mol. %, relative to TMHQ diacetate.

7. The process according to claim 4, wherein 0.1 to 100 ml of solvent/g of TMHQ diacetate is used.

8. The process according to claim 7, wherein 1 to 10 mol of solvent/g of TMHQ diacetate is used.

9. The process according to claim 7, wherein the solvent used is at least one member selected from the group consisting of cyclic or aliphatic carbonate esters of alcohols having a C-1 to C-4 carbon chain, carboxylic acid esters and non-polar solvents.

10. The process according to claim 9, wherein non-polar solvents are aliphatic hydrocarbons or aromatic hydrocarbons.

11. The process according to claim 4, wherein the TMHQ diacetate and isophytol are reacted in a molar ratio of 1:1 to 10:1.

12. The process according to claim 1, wherein the reaction is performed continuously.

13. The process according to claim 1, wherein water of reaction formed during the reaction at least in part remains in the reaction mixture.

14. The process according to claim 1, wherein the esters of the formula (II), the zinc halide and the proton-liberating acid are initially introduced in a solvent and the compound of the formula (III) or (IV) is added thereto.

* * * * *